United States Patent [19]

Opitz et al.

[11] Patent Number: 4,871,738

[45] Date of Patent: Oct. 3, 1989

[54] USE OF 2-PYRIMIDINYL-1-PIPERAZINE DERIVATIVES IN THE TREATMENT OF DEPENDENCE ON NICOTINE

[75] Inventors: Klaus Opitz; Maria-Luise Weischer, both of Muenster; Jörg Traber, Lohmar, all of Fed. Rep. of Germany

[73] Assignee: Troponwerke GmbH & Co. KG, Cologne, Fed. Rep. of Germany

[21] Appl. No.: 262,411

[22] Filed: Oct. 25, 1988

[30] Foreign Application Priority Data

Oct. 31, 1987 [DE] Fed. Rep. of Germany ....... 3736974

[51] Int. Cl.$^4$ .................. A61K 31/50; A61K 31/495
[52] U.S. Cl. .................... 514/252; 514/255; 514/813
[58] Field of Search .................. 514/252, 255, 813

[56] References Cited

U.S. PATENT DOCUMENTS

| | | | |
|---|---|---|---|
| 3,976,776 | 8/1976 | Wu et al. | 514/252 |
| 4,182,763 | 1/1988 | Casten | 514/252 |
| 4,438,119 | 3/1984 | Allen et al. | 514/252 |
| 4,634,703 | 1/1987 | Kurtz et al. | 514/252 |
| 4,640,921 | 2/1987 | Othmer et al. | 514/252 |
| 4,687,772 | 8/1987 | Alderdice | 514/252 |
| 4,777,173 | 10/1988 | Shrotryia et al. | 514/252 |

*Primary Examiner*—Stanley J. Friedman
*Attorney, Agent, or Firm*—Sprung Horn Kramer & Woods

[57] ABSTRACT

A method of treating warm-blooded animals to reduce their dependency upon nicotine comprising administering to such animals a medicament containing a 2-pyrimidinyl-1-piperazine derivative of the formula

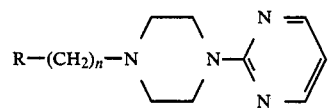

in which n stands for 2, 3, 4, 5 or 6 and R stands for

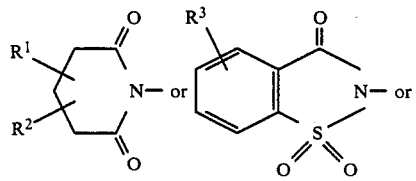

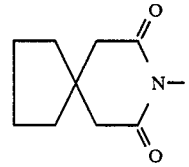

7 Claims, No Drawings

USE OF 2-PYRIMIDINYL-1-PIPERAZINE DERIVATIVES IN THE TREATMENT OF DEPENDENCE ON NICOTINE

The invention relates to the use of 2-pyrimidinyl-1-piperazine derivatives for the preparation of medicaments for the treatment of dependence on nicotine and to corresponding medicaments.

2-Pyrimidinyl-1-piperazine derivatives and their essentially anxiolytic action are known from EP-A 0,129,128. Known active compounds from this class of substances are 8[4-N[4-(2-pyrimidinyl)-1-piperazinyl]-butyl]-8-azaspiro[4,5]-decane-7,9-dione hydrochloride (as given in INN: buspirone, Pharmacol. Biochem. Behav. 23, 687 to 694 (1985)), 4,4-dimethyl-1-[4-[4-(2-pyrimidinyl)-1-piperazinyl]butyl]-2,6-piperidineione hydrochloride (as given in INN: gepirone, Naunyn-Schmiedeberg's Arch. Pharmacol. 335, 454 to 464 (1987)) and 2-(4-(4-(2-pyrimidinyl)-1-piperazinyl)-butyl)-1,2-benzoisothiazol 3(2H)one 1,1-dioxide hydrochloride (as given in INN: ipsapirone, Naunyn-Schmiedeberg's Arch. Pharmacol. 328, 467 to 470 (1985)).

Nictoine dependence manifests itself in the strong desire to smoke, the occurrence of withdrawal symptoms and the inability of most smokers to give up the life-threatening "habit".

Experiments to relieve the compulsive desire to smoke (craving) of dependent smokers in abstinence by oat extracts, lobeline or cytisine met with little success (Dtsch. med. Wschr. 112, 559–564 (1987)). The use of nicotine itself, for example in the form of chewing gum, leads to a moderate improvement in the success rate of breaking the smoking habit (Lancet 2, 27–30 (1987)). This method of breaking the smoking habit is problematical, however, since nicotine is a strong poison and causes dependence (J. Amer. med. Assoc. 255, 3277–3279 (1986)).

The use of 2-pyrimidinyl-1-piperazine derivatives of the formula

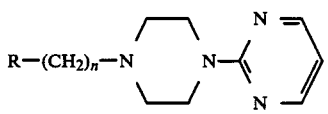

in which
n stands for one of the numbers 2, 3, 4, 5 or 6 and
R stands for one of the radicals

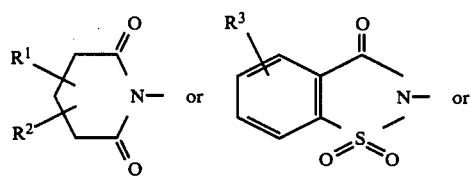

wherein
$R^1$, $R^2$ and $R^3$ are identical or different and
denote hydrogen or lower alkyl and/or their salts has been found for the preparation of medicaments for the treatment of dependence on nicotine.

Corresponding medicaments are characterized in that they contain 2-pyrimidinyl-1-piperazine derivatives of the formula

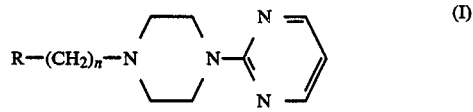

in which
n stands for one of the numbers 2, 3, 4, 5 or 6 and
R stands for one of the radicals

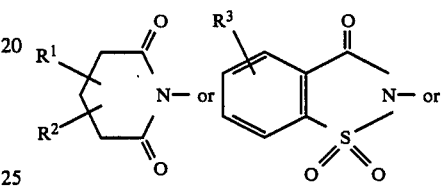

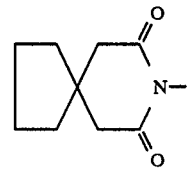

wherein
$R^1$, $R^2$ and $R^3$ are identical or different and
denote hydrogen or lower alkyl and/or their salts.

In the context of the formula (I), lower alkyl in general denotes a straight-chain or branched hydrocarbon radical having 1 to about 6 carbon atoms. Examples which may be mentioned are methyl, ethyl, propyl, isopropyl, butyl, isobutyl, pentyl, isopentyl, hexyl and isohexyl. Methyl and ethyl are preferred.

Preferred 2-pyrimidinyl-1-piperazine derivatives of the formula (I) are those in which
n stands for one of the numbers 3 or 4 and
$R^1$, $R^2$ and $R^3$ denote hydrogen or methyl.

Salts which may be mentioned are pharmacologically acceptable salts, such as the hydrochlorides.

Ipsapirone, gepirone and buspirone and particularly preferred.

The preparation of the 2-pyrimidinyl-1-piperazine derivatives is known per se (DE-A 3,321,969) and can take place, for example, by reaction of suitable benzisothiazoles with (piperazinyl)-pyrimidines.

The medicaments according to the invention in general contain 1 to 15% by weight, preferably 5 to 10% by weight, of 2-pyrimidinyl-1-piperazine derivatives.

Of course, it is possible that the medicaments according to the invention contain further active compounds known per se.

The medicaments according to the invention may be converted in a known manner into the customary formulations, such as tablets, dragees, pills, granules, aerosols, syrups, emulsions, suspensions and solutions, using inert, non-toxic, pharmaceutically suitable excipients or solvents.

The formulations are produced, for example, by extending the active compounds with solvents and/or excipients, if appropriate using emulsifiers and/or dispersants, where, for example, in the case of the use of water as a diluent, organic solvents may be used if appropriate as auxiliary solvents.

Auxiliaries which may be mentioned are, for example: water, non-toxic organic solvents, such as paraffins (for example mineral oil fractions), vegetable oils (for example groundnut/sesame oil), alcohols (for example ethyl alcohol, glycerol), excipients, such as, for example, ground natural minerals (for example kaolins, clays, talc, chalk), ground synthetic minerals (for example highly disperse silica, silicates), sugars (for example sucrose, lactose and dextrose), emulsifiers (for example polyoxyethylene fatty acid esters, polyoxyethylene fatty alcohol ethers, alkylsulphonates and arylsulphonates), dispersants (for example lignin, sulphite waste liquors, methylcellulose, starch and polyvinylpyrrolidone) and lubricants (for example magnesium stearate, talc, stearic acid and sodium lauryl sulphate).

Administration takes place in a customary manner, preferably orally, parentrally, perlingually or intravenously. In the case of oral use, tablets may of course also contain additives, such as sodium citrate, calcium carbonate and dicalcium phosphate together with various additives, such as starch, preferably potato starch, gelatin and the like in addition to the said excipients. Furthermore, lubricants, such as magnesium stearate, sodium lauryl sulphate and talc may additionally be used for tabletting. In the case of aqueous suspensions, various flavor-improvers or colorants may be added to the active compounds in addition to the abovementioned auxiliaries.

In the case of parenteral use, solutions of the active compounds using suitable liquid excipients may be employed. In general, it has proved advantageous in intravenous applications to administer amounts of about 0.001 to 1 mg/kg, preferably about 0.01 to 0.5 mg/kg of body weight to obtain effective results, and in oral applications, the dosage is about 0.01 to 20 mg/kg, preferably 0.1 to 10 mg/kg of body weight.

Nevertheless, it may, if appropriate, be necessary to deviate from the said amounts, depending on the body weight or the type of application route, on the individual behavior towards the medicament, the type of its formulation and the point in time or interval at which administration takes place. Thus, in some cases it may be sufficient to manage with less than the previously mentioned minimum amount, when in other cases the said upper limit must be exceeded. In the case of administration of larger amounts, it may be advisable to divide these into several individual doses throughout the day.

The 2-pyrimidinyl-1-piperazine derivatives according to the invention eliminate the compulsive desire to smoke and therefore facilitate withdrawal from nicotine.

EXAMPLE 1 (Production)

Preparation of 2-(4-(4-(2-pyrimidinyl)-1-piperazinyl)-butyl)-1,2-benzoisothiazol-3(2H)one 1,1-dioxide

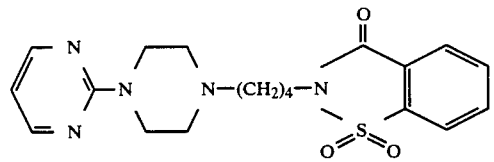

0.02 mol of 2-(4-bromobutyl)-1,2-benzoisothiazol-3-(2H)one 1,1-dioxide and 0.02 mol of 1-(2-pyrimidinyl)-piperazine are stirred with 0.02 mol of $K_2CO_3$ in 150 ml of absolute dimethylformamide (DMF) at 100° C. for 1 hour. The mixture is then concentrated. Water is added and the organic substance is taken up in methylene chloride ($CH_2Cl_2$). The dried $CH_2Cl_2$ phase is added to a silica gel column and eluted using $CH_2Cl_2/CH_3OH$ (95:5).

Yield: 34% of theory; melting point: 138°–139° C.

EXAMPLE 2 (application)

The tested tupaias (*Tupaia belangeri*) on free choice prefer an aqueous nicotine hydrogen tartrate solution (10 mg/l) as opposed to water.

In the test, 10 tupaias have the free choice of taking nicotine. The nicotine solution is offered to the animals in the given concentration once daily on 5 successive days, where they always also have the choice of drinking nicotine-free water. The oral administration of ipsapirone takes place 15 to 30 minutes in each case before the beginning of the nicotine exposure occurring on each of the 5 days.

Table 1 shows the influence of ipsapirone on the voluntary taking of nicotine.

TABLE 1

| Active compound | Dose of active compound (mg/kg p.o.) | N % | Significance |
|---|---|---|---|
| ipsapirone | 15 | −32.3 | $p < 0.0003$ |
| | 30 | −25.9 | $p < 0.0002$ |

N denotes the decrease in nicotine ingestion in percent after treatment compared to the consumption by the untreated animals in the preceding week (100%)

The significances were calculated for paired values with the aid of Student's t-test.

The test shows that the voluntary nicotine consumption decreased considerably after treatment with the active compound.

What is claimed is:

1. A method of treatment to reduce the dependence of warm-blooded animals upon nicotine comprising administering to said nicotine dependent animals a medicament containing an effective amount of at least one 2-pyrimidinyl-1-piperazine derivative of the formula

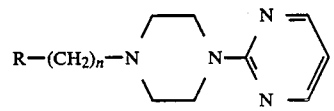

in which
n stands for 2, 3, 4, 5 or 6 and
R stands for

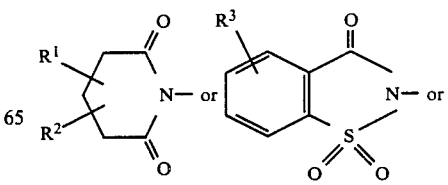

-continued

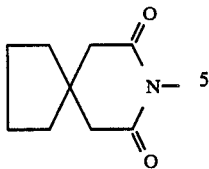

wherein $R^1$, $R^2$, and $R^3$ each independently denote hydrogen or lower alkyl and salts thereof.

2. A method according to claim 1 wherein $R^1$, $R^2$ and $R^3$ each independently denote hydrogen or alkyl having 1 to 6 carbon atoms.

3. A method according to claim 1, wherein n stands for 3 or 4 and $R^1$, $R^2$ and $R^3$ each independently denote hydrogen or methyl.

4. A method according to claim 1, wherein the 2-pyrimidinyl-1-piperazine derivative is 8[4-N[4-(2-pyrimidinyl)-1-piperazinyl]-butyl]-8-azaspiro[4,5]-decane-7,9-dione.

5. A method according to claim 1, wherein the 2-pyrimidinyl-1-piperazine derivative is 4,4-dimethyl-1-[4-[4-(2-pyrimidinyl)-1-piperazinyl]-butyl]-2,6-piperidinedione.

6. A method according to claim 1, wherein the 2-pyrimidinyl-1-piperazine derivative is 2-(4-(4-(2-pyrimidinyl)-1-piperazinyl)-butyl-1,2-benzoisothiazol-3(2H)one 1,1-dioxide.

7. A method according to claim 1, wherein the medicament contains 1 to 15% by weight of 2-pyrimidinyl-1-piperazine derivatives.

* * * * *